United States Patent
Lin et al.

(10) Patent No.: US 9,782,537 B2
(45) Date of Patent: Oct. 10, 2017

(54) PORTABLE INFUSION DEVICE

(71) Applicants: Sheng-Lian Lin, Taoyuan (TW); Yu-Ying Lin, Taoyuan (TW); Tung-Yi Lin, Taoyuan (TW)

(72) Inventors: Sheng-Lian Lin, Taoyuan (TW); Yu-Ying Lin, Taoyuan (TW); Tung-Yi Lin, Taoyuan (TW)

(*) Notice: Subject to any disclaimer, the term of this patent is extended or adjusted under 35 U.S.C. 154(b) by 102 days.

(21) Appl. No.: 14/801,611

(22) Filed: Jul. 16, 2015

(65) Prior Publication Data

US 2016/0331892 A1    Nov. 17, 2016

(30) Foreign Application Priority Data

May 12, 2015    (TW) .............................. 104115112 A

(51) Int. Cl.
*A61M 5/148*    (2006.01)
*A61M 5/152*    (2006.01)
*A61M 5/142*    (2006.01)

(52) U.S. Cl.
CPC ........ *A61M 5/148* (2013.01); *A61M 5/14244* (2013.01); *A61M 5/152* (2013.01)

(58) Field of Classification Search
CPC ... A61M 5/148; A61M 5/152; A61M 5/14244
USPC ....................................................... 224/600
See application file for complete search history.

(56) References Cited

U.S. PATENT DOCUMENTS

| | | | | |
|---|---|---|---|---|
| 3,625,401 A | * | 12/1971 | Terry | A61M 5/148 |
| | | | | 128/DIG. 12 |
| 4,033,479 A | * | 7/1977 | Fletcher | G01F 11/08 |
| | | | | 128/DIG. 12 |
| 4,613,327 A | * | 9/1986 | Tegrarian | A61M 5/1483 |
| | | | | 128/DIG. 12 |
| 5,211,626 A | * | 5/1993 | Frank | A61M 5/148 |
| | | | | 128/DIG. 12 |
| 5,232,439 A | * | 8/1993 | Campbell | A61M 5/148 |
| | | | | 128/DIG. 12 |
| 5,342,313 A | * | 8/1994 | Campbell | A45F 3/20 |
| | | | | 222/103 |
| 5,399,166 A | * | 3/1995 | Laing | A61M 5/1483 |
| | | | | 604/131 |

(Continued)

FOREIGN PATENT DOCUMENTS

CN    202136637 U    2/2012
JP    1996-257121    10/1996
(Continued)

*Primary Examiner* — Peter Helvey
(74) *Attorney, Agent, or Firm* — Li-Jen Shen

(57) ABSTRACT

A portable infusion device adapted to hold an infusion bag is provided. The infusion bag includes a bag body and an infusion tube connected to the bag. The portable infusion device includes a case, a plate and an elevating mechanism. The case includes an accommodating space for accommodating the bag body. The case has an aperture. The infusion tube is adapted to pass through the aperture. The plate is disposed in the receiving space and is adapted to carry the bag body. The elevating mechanism is disposed in the accommodating space and is movably connected to the case. The plate is fixed on the elevating mechanism. The elevating mechanism is adapted to push the plate to move. The portable infusion device is easily carried in use.

6 Claims, 8 Drawing Sheets

(56) References Cited

U.S. PATENT DOCUMENTS

| | | | | |
|---|---|---|---|---|
| 5,411,482 A | * | 5/1995 | Campbell | A61M 5/148 |
| | | | | 604/153 |
| 5,472,420 A | * | 12/1995 | Campbell | A61M 5/148 |
| | | | | 128/DIG. 12 |
| 5,954,696 A | * | 9/1999 | Ryan | A61M 5/1483 |
| | | | | 128/DIG. 12 |
| 6,099,492 A | * | 8/2000 | Le Boeuf | A61M 1/02 |
| | | | | 128/DIG. 12 |
| 2004/0026448 A1 | * | 2/2004 | Pichotte | A61M 5/148 |
| | | | | 222/95 |
| 2013/0237915 A1 | * | 9/2013 | Barrelli | A61M 5/14244 |
| | | | | 604/136 |
| 2014/0276427 A1 | * | 9/2014 | Chi | A61M 5/145 |
| | | | | 604/151 |

FOREIGN PATENT DOCUMENTS

| | | |
|---|---|---|
| JP | 2006-346436 A | 12/2006 |
| TW | 201125604 A1 | 8/2011 |

* cited by examiner

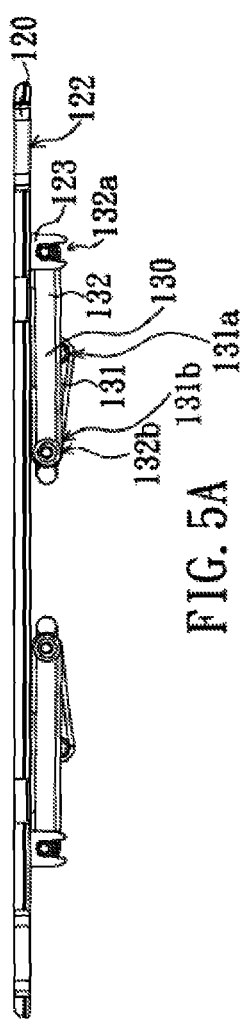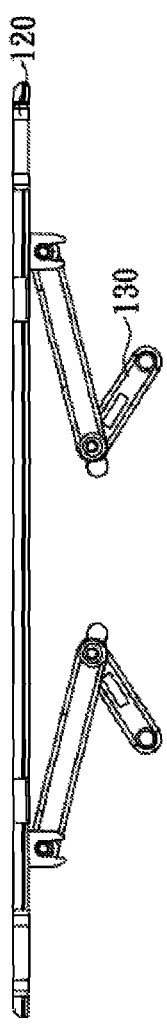
FIG. 5A
FIG. 5B

PORTABLE INFUSION DEVICE

FIELD OF THE INVENTION

The present invention relates to an infusion device, and more particularly to a portable infusion device.

BACKGROUND OF THE INVENTION

When people get sick, treatment include orally taking medication or taking intravenous injections. Intravenous injections inject blood, medicine or nutrition directly to bloodstreams. One method of applying intravenous injections is to use drip bags and allow fluids to slowly infuse into the patients' bodies. During injection, the drip bag must be held at a position higher than the point of injection, such that gravity can be used to inject the fluid into the patient's body.

When using drip bags to inject fluid into a patient's body, the drip bag is usually hung on a hanger such that the drip bag is kept at a high position. However, when the patient needs to walk or move to other places, the hanger needs to be pushed around for hanging the drip bag, or the drip bag needs to be held at a high position by hand, creating inconvenience for the patient.

SUMMARY OF THE INVENTION

The present disclosure provides a portable infusion device which is convenient to carry around.

The present disclosure provides a portable infusion device, configured to accommodate an infusion bag. The infusion bag has a bag body and an infusion tube connected to the bag body. The portable infusion device includes a case, a plate and an elevating mechanism. The case has an accommodating space for accommodating the bag body. The case is formed with an aperture. The infusion tube is configured to pass through the aperture. The plate is disposed in the receiving space for carrying the bag body. The elevating mechanism is disposed in the accommodating space and is movably connected to the case. The plate is fixed on the elevating mechanism. The elevating mechanism is configured to push the plate to move.

In an embodiment of the present disclosure, the elevating mechanism is connected to the plate and a bottom portion of the case opposite the plate.

In an embodiment of the present disclosure, the elevating mechanism includes a first frame, a second frame, a rotation shaft and a torque spring. The first frame has a first side and a second side opposite each other, and the first side is connected to the bottom portion of the case. The second frame has a third side and a fourth side opposite each other, and the third side is connected to the plate. The second side of the first frame and the fourth side of the second frame are pivotally connected to the rotation shaft. The torque spring sleeves the rotation shaft, and has two ends respectively connected to the second side of the first frame and the fourth side of the second frame. The torque spring is configured to rotate the first frame and the second frame with respect to each other, such that the plate elevates away from the bottom portion of the case from a first position to a second position.

In an embodiment of the present disclosure, the portable infusion device further comprises a locking mechanism configured to lock the plate and fix the plate at the first position.

In an embodiment of the present disclosure, a surface of the plate facing the bottom portion of the case is formed with an engagement portion. The locking mechanism comprises a fixing element, a compression spring, a movable engagement element and a movable locking element, wherein the fixing element if fixed to the bottom portion of the case and has a side wall. One end of the compression spring abuts the side wall. The movable engagement element has a second engagement portion, and another end of the compression spring abuts the movable engagement portion. As the plate moves from the second position to the first position, the first engagement portion pushes the second engagement portion, driving the movable engagement element to move toward the side wall in a first direction and compress the compression spring. When the plate moves to the first position, the first engagement portion releases the second engagement portion, and the compression spring pushes the second engagement portion to move in a second direction opposite to the first direction, to engage the first engagement portion. The movable locking element abuts the movable engagement element, and is configured to move to a locking position and a release position. When the movable locking element moves from the locking position to the release position, the movable locking element pushes the movable engagement element to move in the first direction to release the engagement between the first engagement portion and the second engagement portion.

In an embodiment of the present disclosure, an inner wall of the case is formed with a plurality of guide rail, for guiding the plate to move along the guide rails.

In an embodiment of the present disclosure, the case includes a bottom box and a cover. The bottom box has an opening. The cover is pivotally connected to the bottom box for covering the opening.

In an embodiment of the present disclosure, the case further comprises a locking element arranged at a side wall of the bottom box for fixing the cover to the bottom box.

In an embodiment of the present disclosure, the side wall of the case is formed with a window proximal to a top portion of the case opposite the plate.

In an embodiment of the present disclosure, the portable infusion device further comprises a shoulder strap, and the case is formed with a plurality of hanging elements for the strap to be coupled to.

The portable infusion device can drive the plate through the movable elevating mechanism, to press the bag of the infusion bag carried by the plate. By this configuration, the infusion bag does not need to be held a high position in order to inject the fluid in the infusion bag into a patient's body. Therefore, the portable infusion device of the present disclosure is more portable.

The present invention will become more readily apparent to those ordinarily skilled in the art after reviewing the following detailed description and accompanying drawings.

BRIEF DESCRIPTION OF THE DRAWINGS

FIG. 5A and FIG. 5B show schematic diagrams of an elevating mechanism pushing a plate to move according to an embodiment of the present disclosure;

DETAILED DESCRIPTION OF PREFERRED EMBODIMENTS

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
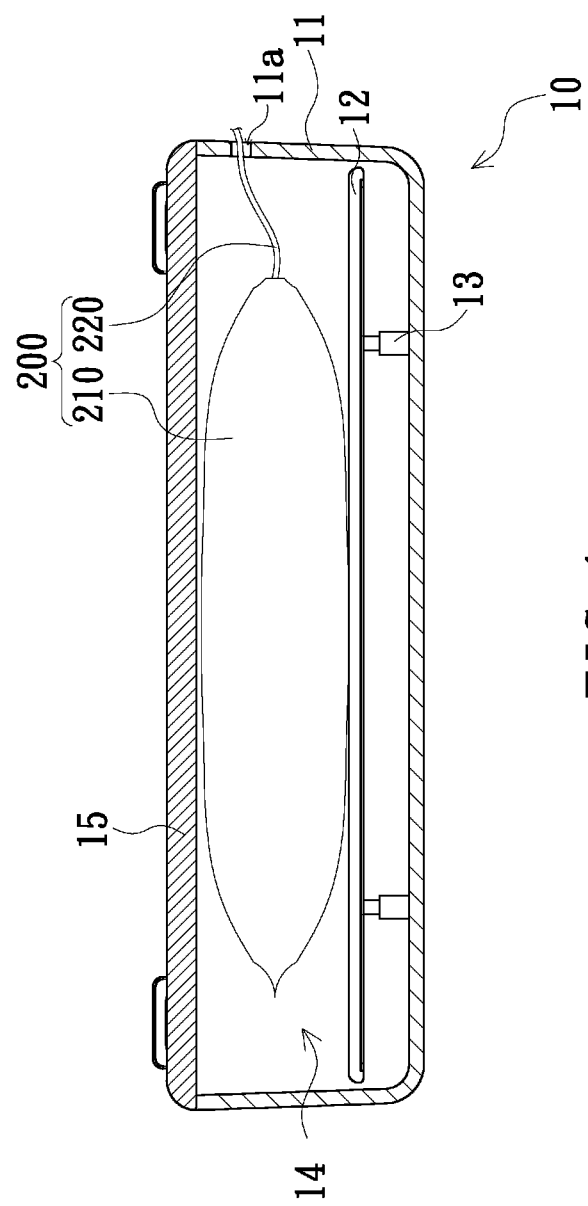
FIG. 1 shows a schematic diagram of a portable infusion device and an infusion bag according to a first embodiment of the present disclosure.

FIG. 1 is a schematic cross-sectional diagram of a portable infusion device and an infusion bag according to an embodiment of the present disclosure. Referring to FIG. 1, a portable infusion device 10 in the present embodiment is configured to accommodate an infusion bag 200. The infusion bag 200 has a bag body 210 and an infusion tube 220 connected to the bag body 210. The portable infusion device 10 includes a case 11, a plate 12 and an elevating mechanism 13. The case 11 has an accommodating space 14 for accommodating the bag body 210. The case 11 includes an aperture 11a. The infusion tube 220 is configured to pass through the aperture 11a and extend out of the case 11. The plate 12 is disposed in the accommodating space 14, and is configured to carry the bag body 210. The elevating mechanism 13 is disposed in the accommodating space 14, and is movably connected to the case 11. The plate 12 is fixed on the elevating mechanism 13. The elevating mechanism 13 is configured to push the plate 12 to move.

Regarding the portable infusion device 10 of the present embodiment, the movable elevating mechanism 13 can push the plate 12 to move upward and the bag body 210 of the infuse ion bag 200 abuts a top wall 15 of the case 11, therefore when the plate 12 moves upward, the bag body 210 of the infusion bag 200 is pressed and the fluid in the bag body 210 flows out through the infusion tube 220. By this configuration, the infusion bag 200 does not need to be held at a position higher than the point of injection in order for fluid inside the infusion bag 200 to be injected into a patient's body. Therefore the portable infusion device 10 of the present embodiment is easy to carry around.

In the present disclosure, the structures of the elevating mechanism, the case and the plate of the portable infusion device can be embodied by different implementations. The following describes the structure and operation of another embodiment of the portable infusion device of the present disclosure. Of particular note, the following is only one embodiment of the portable infusion device of the present disclosure, and is not meant to be limiting.

Figure 2:
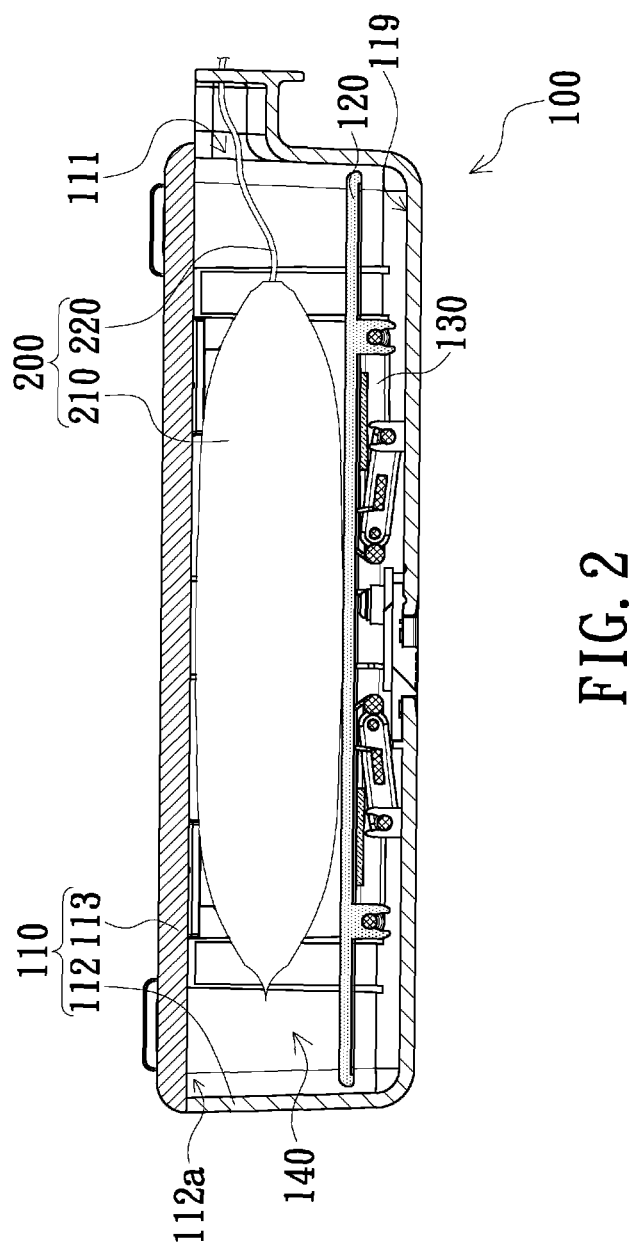
FIG. 2 shows a cross-sectional view of a portable infusion device and an infusion bag according to another embodiment of the present disclosure.
Figure 3:
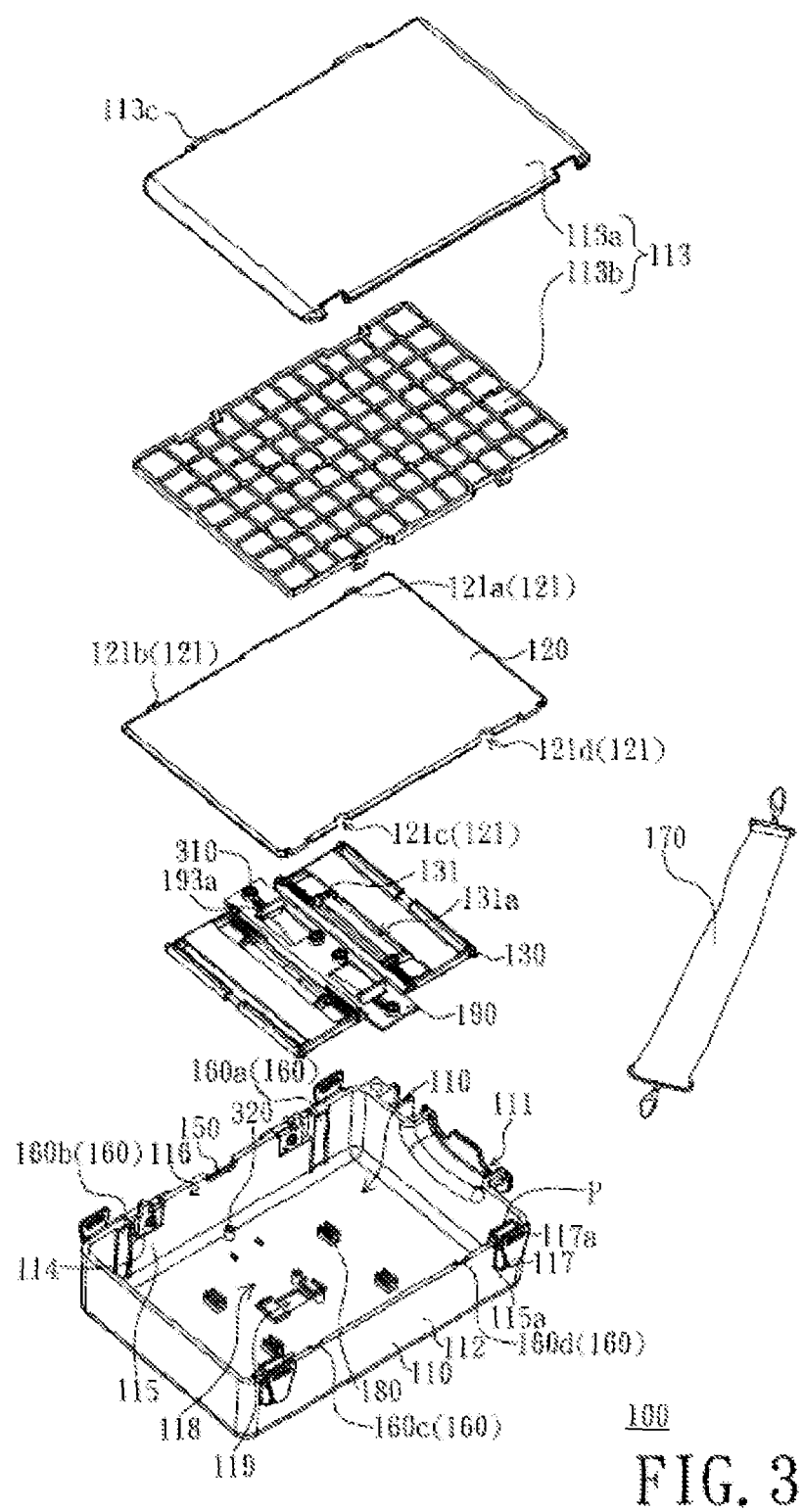
FIG. 3 shows an exploded view of the portable infusion device of FIG. 2.

FIG. 2 shows a cross-sectional diagram of a portable infusion device and an infusion bag according to another embodiment of the present disclosure. FIG. 3 shows an exploded view of the portable infusion device of FIG. 2. Referring to FIG. 2 and FIG. 3, the portable infusion device 100 of the present embodiment includes a case 110, a plate 120 and an elevating mechanism 130. The case 110 includes for example a bottom box 112 and a cover 113. The bottom box 112 has an opening 112a. In the present embodiment, the opening 112a of the bottom box 112 is for example arranged at a side of the bottom box 112 opposite to the plate 120, but the present disclosure is not limited thereto. For example, in other embodiments, the opening 112a of the bottom box 12 can also be arranged at a side adjacent to a bottom portion 118 of the bottom box 112.

In the present embodiment, the cover 113 is pivotally connected to the bottom box 112 at a location of the opening 112a, and is configured to cover the opening 112a. The cover 113 and the bottom box 112 define an accommodating space 140 therebetween. When the cover 113 is opened, the infusion bag 200 can be disposed into the accommodating space 140 through the opening 112a. The bottom box 112 has an aperture 111, such that the infusion tube 220 of the infusion bag 200 can extend out of the case 110 through the aperture 111. Additionally, after the cover 113 is closed and when the elevating mechanism 130 pushes the plate 120 to move upward, the cover 113 can resist the bag body 210 carried on the plate 120, thereby together with the plate 120 pressing the bag body 210, such that the fluid inside the bag body 210 flows out through the infusion tube 220. As shown in FIG. 3, the cover 113 of the present embodiment includes for example two boards 113a, 113b which can be joined together, wherein the board 113b is configured to press the bag body 210, and the board 113a is configured to cover the board 113b. In other embodiments, the cover 113 can be a single board or constituted by three or more boards.

Additionally, referring to FIG. 3, the case 110 for example includes a locking element 114 arranged at an end of a side wall 115 of the bottom box 112 proximal to the opening 112a and opposite to a pivot P of the cover 113 and the bottom box 112. The locking element 114 is configured to move between a locking position and a release position. In the present embodiment, the board 113a of the cover 113 has for example an engagement portion 113c. When the cover 113 is closed, the locking element 114 and the engagement portion 113c engage each other, thereby locking the cover 113 to the bottom box 112. When a user pushes the locking element 114 from the locking position to the release position, the locking element 114 and the engagement portion 113c disengage, and the user can open the cover 113. The locking element 114 can have elastic portions, such that the locking element 114 can automatically restore to the locking position when no force is applied thereto. Additionally, the locking element 114 of the present embodiment amounts to two for example, and the amount of the engagement portions 113c matches that of the locking elements 114, but the present disclosure does not limit the amount of the locking elements 114.

In the present embodiment, the side wall 115 of the case 110 for example is formed with a window 150 proximal to a top portion of the case 110 opposite the plate 120. In other words, the window 150 is positioned at the side wall 115 of the bottom box 112 and is proximal to the cover 113. The arrangement of the window 150 allows the user to view the amount of fluid remaining in the infusion bag 200, so as to timely replace the infusion bag 200 or stop the injection. In another embodiment, the bottom box 112 of the case 110 can be made of a transparent material, such that the amount of fluid remaining in the infusion bag 200 is observable without the window 150.

Additionally, an inner wall 116 of the case 110 is for example formed with a plurality of guide rail 160, and the plate 120 for example includes a plurality of guide elements 121. The guide elements 121 and the guide rails 160 work together, such that the plate 120 move along the guide rails 160 without being offset. In the present embodiment, the amount of the guide rails 160 is for example four, wherein two of the guide rails 160a, 160b are recessed rails, and the other two guide rails 160c, 160d are protruding rails. The amount of the guide elements 121 of the plate 120 corresponds to the amount and shapes of the guide rails 160. In other words, the amount of the guide elements 121 of the present embodiment is four, wherein the two guide elements 121a, 121b are protruding elements corresponding to the recessed guide rails 160a, 160b, and the other two guide elements 121c, 121d are recessed elements corresponding to the protruding guide rails 160c, 160d. However, the present disclosure does not limit the amount and shape of the guide rails 160 and the guide elements 121.

As shown in FIG. 3, the portable infusion device 100 of the present embodiment for example further includes a shoulder strap 170. In the present embodiment, the case 110 for example further includes a plurality of hanging elements 117 joined to the bottom box 112. For example, the amount of hanging elements 117 is four, wherein each of the hanging elements 117 has a hanging hole 117a, but the present disclosure does not limit the amounts of the hanging elements 117 and the hanging holes 117a. In other embodiments, the hanging hole 117a can be holes formed on the sidewalls 115 of the case 110. The side wall 115 of the case 110 of the present embodiment has joining elements 115a, such that the hanging elements 117 are joined to the joining elements 115a to fix the hanging elements 117 to the side wall 115 of the case 110. According to different needs, the present disclosure does not limit the method of fixing the hanging elements 117 to the case 110. The hanging holes 117a of the hanging elements 117 provide the shoulder strap 170 to pass through, such that the user can use the shoulder strap 170 to carry the portable infusion device 100.

Figure 4:
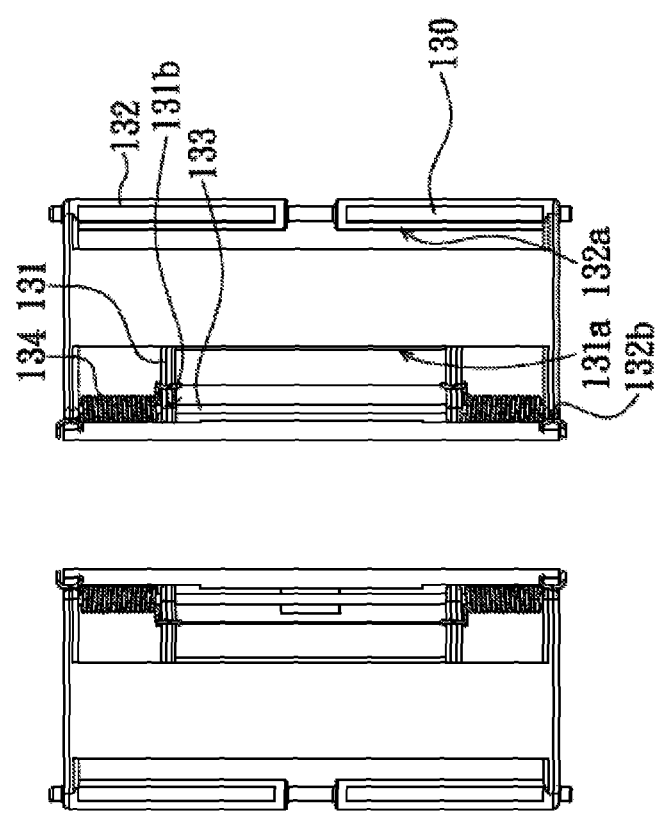
FIG. 4 shows a top view of an elevating mechanism of FIG. 2.

FIG. 4 shows a top view of the elevating mechanism of FIG. 2. Referring to FIG. 3 and FIG. 4, in the present embodiment, the elevating mechanism 130 is connected to the plate 120 and the bottom portion 118 of the case 110 opposite to the plate 120 (as shown in FIG. 3). The elevating mechanism 130 includes a first frame 131, a second frame 132, a rotation shaft 133 and a torque spring 134. In the present embodiment, the elevating mechanisms 130 amount to for example two and are arranged symmetrically at two sides, but are not limited thereto. The first frame 131 has a first side 131a and a second side 131b opposite to each other, wherein the first side 131a is connected to the bottom portion 118 of the case 110 (as shown in FIG. 3). Specifically, the first side 131a of the first frame 131 is for example a column structure, the bottom portion 118 of the case 110 has for example a plurality of first gripping element 180, such that the first side 131a of the first frame 131 can be coupled to the first gripping elements 180, thereby connecting the elevating mechanism 130 to the bottom portion 118 of the case 110. The present embodiment uses for example two first gripping elements 180 to grip the first side 131a of each of the first frames 131, thereby being coupling with the first frame 131. However, the present disclosure does not limit the method of connection between the first frame 131 and the bottom portion 118 of the case 110, nor the amount of the first gripping elements 180.

As shown in FIG. 4, the second frame 132 has a third side 132a and a fourth side 132b, wherein the third side 132a is connected to the plate 120. The second side 131b of the first frame 131 and the fourth side 132b of the second frame 132 are pivotally connected to the rotation shaft 133, and the torque spring 134 sleeves the rotation shaft 133. Two ends of the torque spring 134 are respectively connected to the second side 131b of the first frame 131 and the fourth side 132b of the second frame 132. In the present embodiment, the torque spring 134 for example amounts to two, and are arranged at two ends of the rotation shaft 133.

FIG. 5A and FIG. 5B show schematic diagrams of an elevating mechanism pushing a plate to move according to an embodiment of the present disclosure. Referring to FIG. 5A, when the elevating mechanism 130 is at a state of contraction, the plate 120 is positioned at a first position most proximal to the bottom portion 118 of the case 110 of FIG. 2. As shown in FIG. 5B, when the elevating mechanism 130 is released, the torque spring 134 (shown in FIG. 4) connected to the second side 131b of the first frame 131 and the fourth side 132b of the second frame 132 is configured to rotate the first frame 131 and the second frame 132 with respect to each other, such that the first frame 131 and the second frame 132 gradually open up, thereby elevating the plate 120 from the first position (as shown in FIG. 5A) away from the bottom portion 118 of the case 110 to a second position (as shown in FIG. 5B), so as to push the infusion bag 200 to infuse liquid. The following describes how to set the elevating mechanism 130 to a state of contraction.

Additionally, in the present embodiment, the third side 132a of the second frame 132 is for example a column structure (as shown in FIG. 3). A surface 122 of the plate 120 facing the bottom portion 118 of the case 110 has for example a plurality of second gripping element 123 configured to grip the third side 132a of the second frame 132, such that the plate 120 and the second frame 132 are securely connected. The present disclosure does not limit the method of connection between the second frame 132 and the plate 120, nor the amount of the second gripping elements 123.

Figure 6:
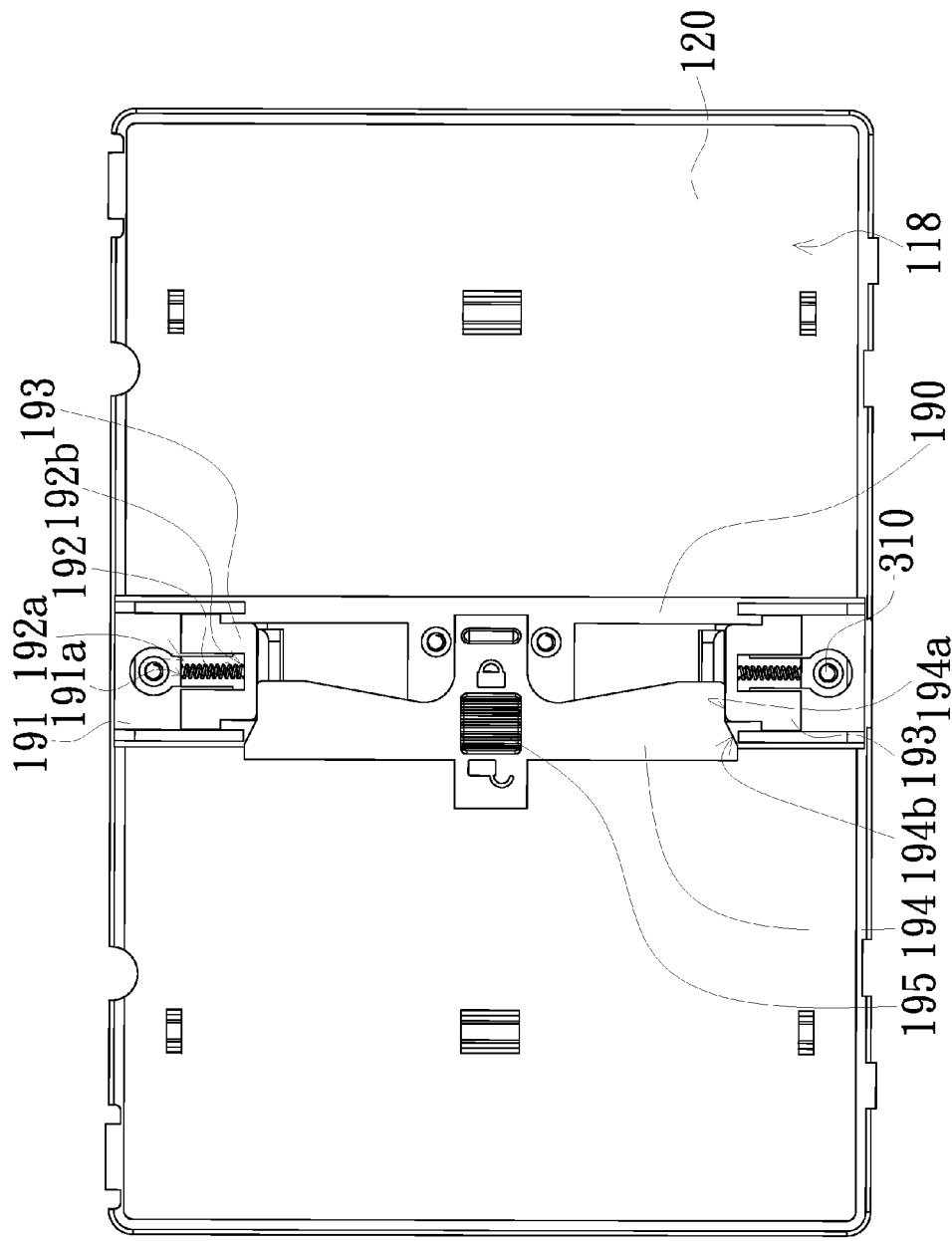
FIG. 6 shows a bottom view of a locking mechanism and a plate of FIG. 3.

FIG. 6 shows a bottom view of a locking mechanism and a plate of FIG. 3. Referring to FIG. 6, the portable infusion device of the present embodiment for example further includes a locking mechanism 190, configured to engage the plate 120 such that the elevating mechanism 130 is held at the state of contraction. In other embodiments, other locking mechanisms can be used to directly engage the elevating mechanism 130, such that the elevating mechanism 130 is held at the state of contraction.

In the present embodiment, the locking mechanism 190 includes a fixing element 191, a compression spring 192, a movable engagement element 193 and a movable locking element 194, wherein the fixing element 191 is fixed to the bottom portion 118 of the case 110 of FIG. 3. The fixing element 191 is for example fixed to the bottom portion 118 of the case 110 by screws 310, wherein the bottom portion 118 of the case 110 is formed with corresponding screw holes 320 (as shown in FIG. 3). The present disclosure does not limit the method of fixing the fixing element 191 to the bottom portion 118 of the case 110.

The fixing element 191 has a side wall 191a, and one end 192a of the compression spring 192 abuts the side wall 191a, and another end 192b of the compression spring 192 abuts the movable engagement element 193. The movable locking element 194 abuts the movable engagement element 193 and includes for example a pushing element 195. The bottom portion 118 of the case 110 is formed with an aperture 119 (as shown in FIG. 3), wherein the pushing element 195 passes through the aperture 119, thereby allowing an user to push the pushing element 195 to move the movable locking element 194 to a locking position or a release position.

In the present embodiment, one end of the movable locking element 194 proximal to the movable engagement element 193 has a first portion 194a and a second portion 194b, wherein the first portion 194a for example abuts a planar surface of the movable engagement element 193, and the second portion 194b is inclined with respect to the first portion 194a.

Figure 7:
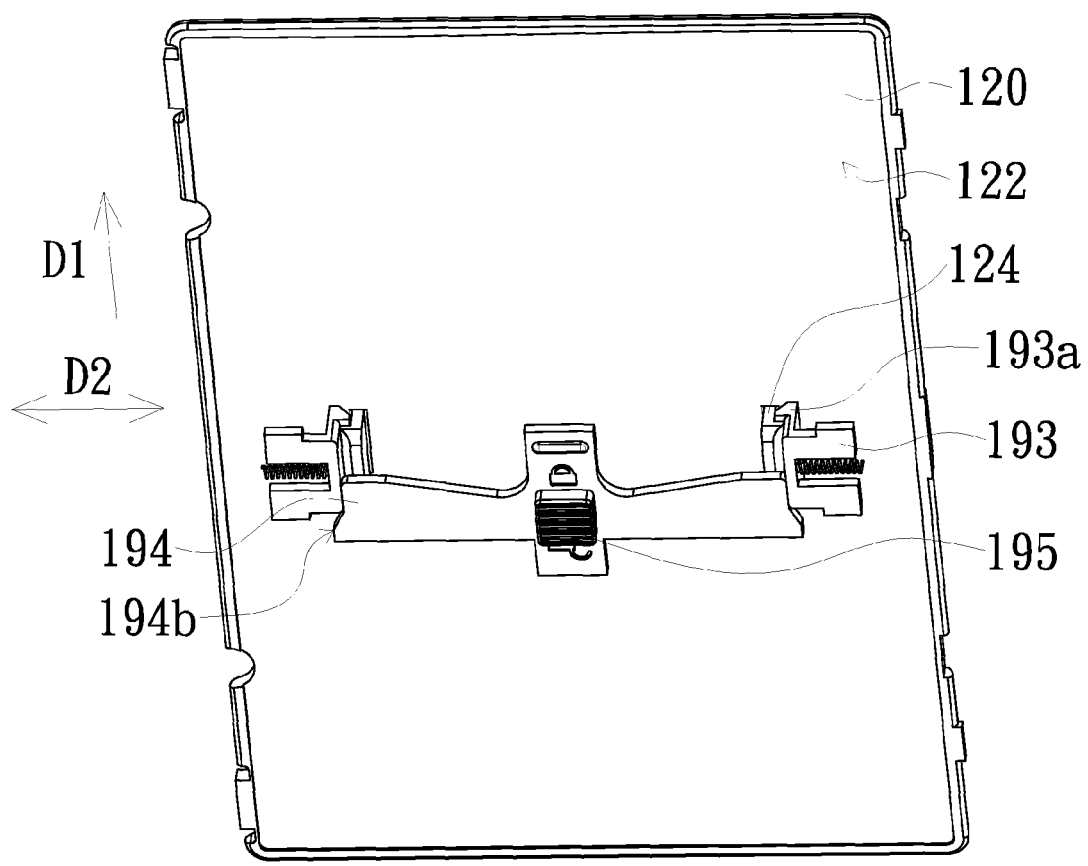
FIG. 7 shows a perspective view of a plate fixed by a locking mechanism according to an embodiment of the present disclosure.

FIG. 7 shows a perspective view of a plate fixed by a locking mechanism according to an embodiment of the present disclosure. In order to avoid cluster, FIG. 7 omits the fixing element 191 of the locking mechanism. FIG. 8A shows a cross-sectional view of a first engagement portion and a second engagement portion of FIG. 7. Referring to FIG. 7 and FIG. 8A, in the present embodiment, the surface 122 of the plate 120 facing the locking mechanism has a first engagement portion 124, the movable engagement element 193 has a second engagement portion 193a, and the first engagement portion 124 and the second engagement portion 193a are for example similarly shaped and oppositely arranged. As shown in FIG. 8A, the first engagement portion 124 includes a first abutting portion 124a and a first inclined portion 124b inclined with respect to the first abutting portion 124a, and the second engagement portion 193a also has a second abutting portion 193b and a second inclined portion 193c inclined with respect to the second abutting portion 193b. The first engagement portion 124 and the second engagement portion 193a engage with each other through the first abutting portion 124a and the second abutting portion 193b, thereby fixing the elevating mechanism 130 at the state of contraction. However the present disclosure does not limit the method of engagement of between the first engagement portion 124 and the second engagement portion 193a.

Figure 8B:
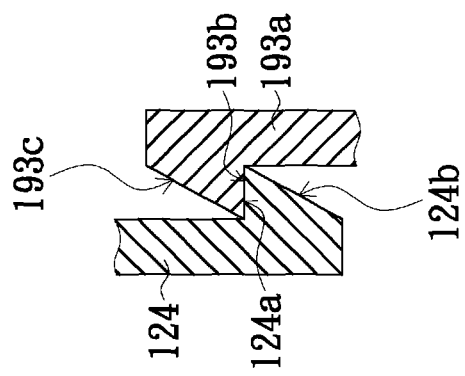
FIG. 8B shows a cross-sectional view of a first engagement portion and a second engagement portion moving relative to each other according to an embodiment of the present disclosure.
Figure 8A:
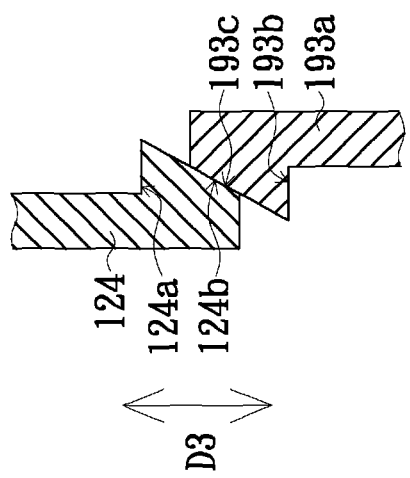
FIG. 8A shows a cross-sectional view of a first engagement portion and a second engagement portion of FIG. 7.

FIG. 8B shows a cross-sectional view of a first engagement portion and a second engagement portion moving relative to each other according to an embodiment of the present disclosure. Referring to FIG. 7 and FIG. 8, when the elevating mechanism 130 is to be elevated, a user can push the pushing element 195 in a first direction D1 to move the movable locking element 194 from the locking position to the release position. During pushing, the second portion 194b of the movable locking element 194 pushes the movable engagement element 193, such that the movable locking element 194 pushes the movable engagement element 193 in a second direction D2 to move outward and compress the compression spring 192, thereby disengaging the first engagement portion 124 and the second engagement portion 193a from each other. At this moment the elevating mechanism 130 is released, and pushes the board 120 and the first engagement portion 124 thereof to move upward in the direction D3. When the first engagement portion 124 and the second engagement portion 193a are separated, the compression spring 192 pushes the movable engagement element 193 back to an original position, and the movable engagement element 193 pushes the movable locking element 194 from the release position to the locking position.

On the other hand, when pressing the plate 120 to move the plate 120 from the second position (as shown in FIG. 5B) to the first position (as shown in FIG. 5A), the first engagement portion 124 moves downward in the direction D3, and the first inclined portion 124b pushes downward on the second inclined portion 193c of the second engagement portion 193a, thereby pushing the movable engagement element 193 to move outward in the direction D2 and compress the compression spring 192. When the first inclined portion 124 and the second inclined portion 193c are separated, the compression spring 192 pushes the movable engagement element 193 in the direction D2 inward toward an original position, such that the second engagement portion 193a engages the first abutting portion 124a of the first engagement portion 124 through the second abutting portion 193b, and such that the movable locking element 194 moves to the locking position for fixing the plate 120 at the first position (as shown in FIG. 5A).

In summary, the portable infusion device 100 of the present disclosure can apply pressure to the infusion bag 200 carried by the plate 120 through movement of the plate 120 pushed by the elevating mechanism 130. When a user uses the infusion bag 200 for infusing liquid, the infusing bag 200 does not need to be held at a high position in order for fluid in the infusion bag 200 to be injected into the patient's body, allowing the user to carry the infusion bag 200 by using the portable infusion device 100. Therefore, the portable infusion device of the present disclosure is easier to carry around.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A portable infusion device for accommodating an infusion bag, the infusion bag comprising a bag body and an infusion tube connected to the bag body, the portable infusion device comprising:
   a case having an accommodating space for accommodating the bag body, wherein the case comprises an aperture, and the infusion tube is configured to pass through the aperture;
   a plate disposed in the accommodating space, configured to carry the bag body and comprising a surface facing a bottom portion of the case, wherein the surface has a first engagement portion; and
   an elevating mechanism disposed in the accommodating space, wherein the elevating mechanism comprises:
     a first frame having a first side and a second side opposite each other, wherein the first side is connected to a bottom portion of the case;
     a second frame having a third side and a fourth side opposite each other, wherein the third side is connected to the plate;
     a rotation shaft, wherein the second side of the first frame and the fourth side of the second frame are pivotally connected to the rotation shaft; and
     a torque spring sleeving the rotation shaft, wherein two ends of the torque spring are respectively connected to a position between the first side and the second side of the first frame and the fourth side of the second frame, the torque spring is configured to rotate the first frame and the second frame with respect to each other, thereby elevating the plate from a first position to a second position away from the bottom portion of the case;
   a locking mechanism configured to lock the plate, thereby fixing the plate at the first position, wherein the locking mechanism comprises:
     a fixing element fixed to the bottom portion of the case and having a side wall;
     a compression spring, wherein one end of the compression spring abuts the side wall;

a movable engagement element having a second engagement portion, wherein another end of the compression spring abuts the movable engagement element, when the plate moves from the second position to the first position, the first engagement portion pushes the second engagement portion to push the movable engagement element toward the side wall in a first direction and compress the compression spring, when the plate reaches the first position, the first engagement portion release the second engagement portion, and the compression spring pushes the second engagement portion to move in a second direction opposite to the first direction for engaging to the first engagement portion; and a movable locking element abutting the movable engagement element and configured to move to a locking position and a release position, wherein when the movable locking position moves from the locking position to the release position, the movable locking element pushes the movable engagement element to move in the first direction for disengaging the first engagement portion and the second engagement portion from each other.

2. The portable infusion device according to claim 1, wherein an inner wall of the case is formed with a plurality of guide rail for guiding the plate to move along the guide rails.

3. The portable infusion device according to claim 1, wherein the case includes a bottom box and a cover, the bottom box has an opening, and the cover is pivotally connected to the bottom box and configured to cover the opening.

4. The portable infusion device according to claim 3, wherein the case further comprises a locking element arranged at a side wall of the bottom box for fixing the cover to the bottom box.

5. The portable infusion device according to claim 1, wherein a side wall of the case is formed with a window, and the window is proximal to a top portion of the case opposite the plate.

6. The portable infusion device according to claim 1, further comprising a shoulder strap, wherein the case has a plurality of hanging hole for the shoulder strap to pass through.

* * * * *